United States Patent
Huang et al.

(10) Patent No.: US 9,681,827 B2
(45) Date of Patent: Jun. 20, 2017

(54) SYSTEMS, METHODS, APPLICATIONS FOR SMART SENSING, MOTION ACTIVITY MONITORING, AND MOTION ACTIVITY PATTERN RECOGNITION

(71) Applicant: LEDO Network, Inc., San Jose, CA (US)

(72) Inventors: Bryan He Huang, San Jose, CA (US); Hong Wang, Cupertino, CA (US)

(73) Assignee: LEDO Networks, Inc., San Jose, CA (US)

(*) Notice: Subject to any disclaimer, the term of this patent is extended or adjusted under 35 U.S.C. 154(b) by 490 days.

(21) Appl. No.: 14/506,633

(22) Filed: Oct. 4, 2014

(65) Prior Publication Data

US 2015/0100245 A1    Apr. 9, 2015

Related U.S. Application Data

(60) Provisional application No. 61/889,012, filed on Oct. 9, 2013, provisional application No. 61/888,953, filed on Oct. 9, 2013.

(51) Int. Cl.
| | |
|---|---|
| *G01D 1/00* | (2006.01) |
| *A61B 5/11* | (2006.01) |
| *G06F 11/30* | (2006.01) |
| *A61B 5/00* | (2006.01) |

(52) U.S. Cl.
CPC .......... *A61B 5/1118* (2013.01); *A61B 5/0022* (2013.01); *A61B 5/1123* (2013.01); *A61B 5/0024* (2013.01); *A61B 5/7267* (2013.01); *A61B 2560/0242* (2013.01); *A61B 2562/0219* (2013.01); *A61B 2562/0223* (2013.01)

(58) Field of Classification Search
CPC .................................................. A61B 5/1118
See application file for complete search history.

(56) References Cited

U.S. PATENT DOCUMENTS

| | | | |
|---|---|---|---|
| 8,849,610 B2* | 9/2014 | Molettiere | A61B 5/1112 |
| | | | 702/160 |
| 2012/0083705 A1* | 4/2012 | Yuen | A61B 5/0002 |
| | | | 600/508 |

* cited by examiner

*Primary Examiner* — Phuong Huynh
(74) *Attorney, Agent, or Firm* — SV Patent Service

(57) ABSTRACT

A computer-implemented method for recognizing a user's activity pattern includes pre-storing activity data in a computer system, automatically determining locations of one or more sensors on a user's body, obtaining time series of measured activity parameters by the one or more sensors, automatically segmenting the time series of measured activity parameters into two or more activity periods, determining a spatial range of the movement in an activity period, and recognizing an activity in the activity period based at least in part on the measured activity parameters and the pre-stored activity data.

20 Claims, 17 Drawing Sheets

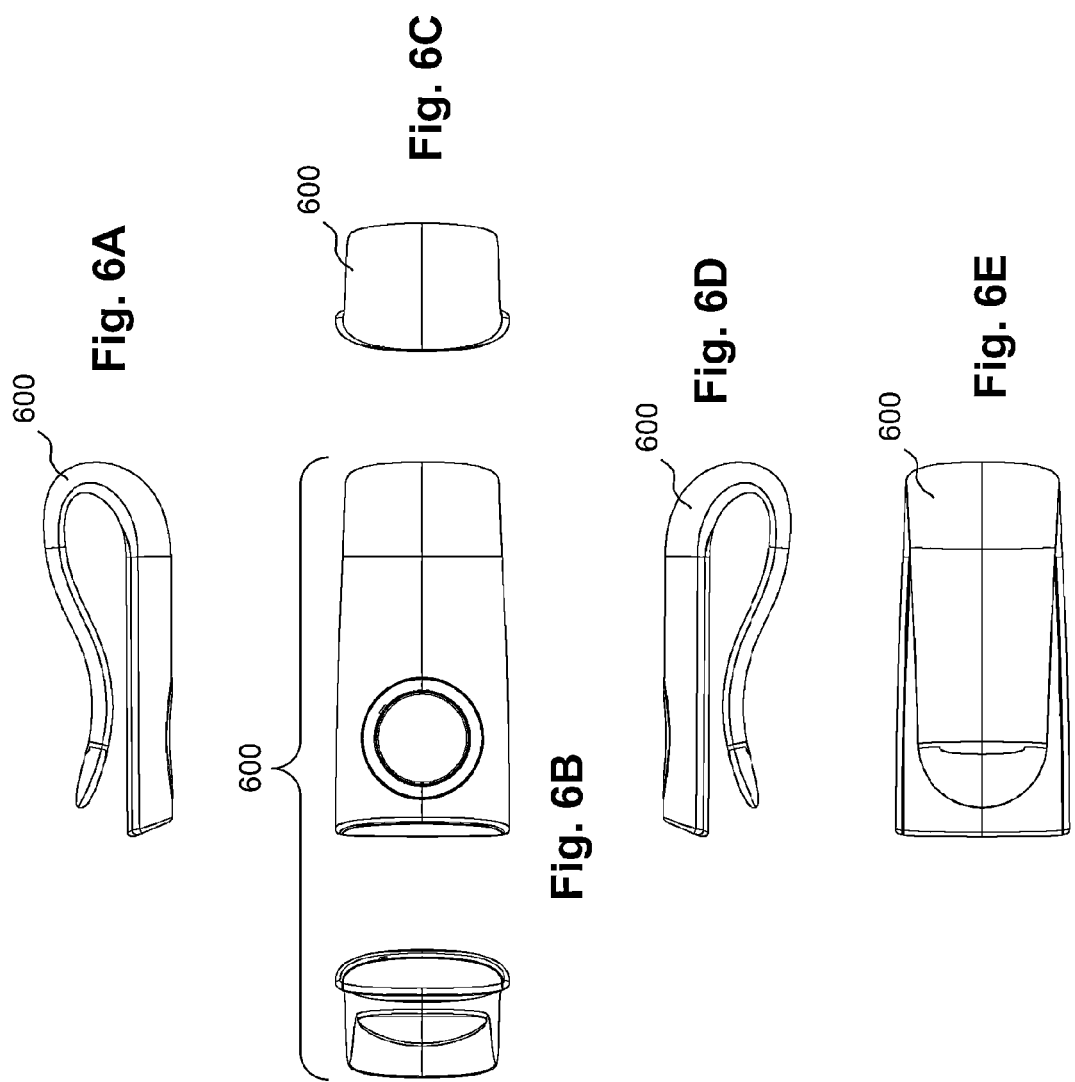

Raw Activity Data 310
- Accelerometer Raw Data 311
- and / or
- Gyroscope Raw Data 312
- and / or
- Magnetometers Raw Data 313
- and / or
- Raw Data from Other Activity Detectors 314

Figure 9B

Activity Patterns 330
- Walking (ground) 331
- Running (ground) 332
- Sitting 333
- Lying Down 334
- Standing 335
- Hiking (upwards) 336
- Hiking (downwards) 337
- Bicycling 338
- ...
- Other Sports 339

Figure 9A

SYSTEMS, METHODS, APPLICATIONS FOR SMART SENSING, MOTION ACTIVITY MONITORING, AND MOTION ACTIVITY PATTERN RECOGNITION

BACKGROUND OF THE INVENTION

The present application relates to technologies for sensing and monitoring motion.

Wearable wireless sensors can exist in different forms, such as clip-like, pin-like, watch-like, and band-shaped devices.

Although various dedicated sensors have been developed, there is a still need for sensors and supporting systems that can have real impact in improving people lives.

SUMMARY OF THE INVENTION

The present application discloses a wireless sensor which includes a housing for attachment to an object, including, but not limited to, a person, an animal, a bird, an aquatic organisms/water product, a plant, a building, a machine system or module, etc.; at least one motion activity detector disposed within the housing; and a processor disposed within the housing, for processing signals from the detectors to assess activity of the object and capturing raw activity data from the detectors for further activity pattern recognition purpose.

A server provides detailed activity log of an object and activity performance comparison between multiple objects via a data network, and to recognize activity patterns of an object using raw activity data from the detectors and calculated activity metrics data from a sensor.

A method recognizes activity patterns of the object based on recognition models and capturing raw activity data from the detectors and calculated activity metrics data from a sensor, wirelessly communicated from the sensor.

In one general aspect, the present invention relates to a computer-implemented method for recognizing a user's activity pattern, comprising: pre-storing activity data in a computer system; automatically determining locations of one or more sensors on a user's body; obtaining time series of measured activity parameters by the one or more sensors; automatically segmenting the time series of measured activity parameters into two or more activity periods; determining a spatial range of the movement in an activity period; and recognizing an activity in the activity period based at least in part on the measured activity parameters and the pre-stored activity data.

Implementations of the system may include one or more of the following. The step of determining locations can include computing Euler angles or Quaternion angles of the one or more sensors to determine locations of one or more sensors on the user's body. The step of automatically segmenting the time series of measured activity parameters can include calculating a first average speed in a first time period; calculating a second average speed in a second time period; and separating the first period and the second period into different activity periods if a ratio of the first average speed to the second average speed is higher than a predetermined threshold. The predetermined threshold can be between 2 and 3. The step of automatically segmenting the time series of measured activity parameters can include calculating a first average acceleration in a first time period; calculating a second average acceleration in a second time period; and separating the first period and the second period into different activity periods if a ratio of the first average acceleration to the second average acceleration is higher than a predetermined threshold. The activity can be recognized in the activity period based in part on the spatial range of the movement in the activity period. The method can further include extracting a signature pattern using the time series of measured activity parameters, wherein the activity data pre-stored in the computer system can include a plurality of signature patterns each corresponding to a known activity, wherein the activity in the activity period can be recognized in part by matching the signature pattern extracted using the time series of measured activity parameters to the one of the plurality of signature patterns stored in the computer system. The signature pattern can be personalized and specific to the user's behavior in the activity. The measured activity parameters can include movement parameters including positions, displacements, distances, speeds, angular velocities, or altitude, physiological parameters including body temperature, heart rate, pulse rate, beat-to-beat heart variability, blood pressure, body fat, or calorie, or environmental characteristics including such as ambient temperature, humility, air quality, light intensity, water quality, sound quality, location. The activity recognized in the activity period can include walking, running, stair climbing, mountain climbing, hiking, driving, taking elevator, dancing, playing soccer, basketball, tennis or ping pong, swimming, diving, sleeping, sitting, driving, jumping, or rotating. The method can further include based on the activity recognized in the activity period, sending control data from the computer system to control an actuator in the sensor, which guides the user to adjust his or her movements. The actuator can produce sound, music, voice, light, vibrations, or heat to guide the user to adjust his or her movements.

In another general aspect, the present invention relates to a computer system for recognizing a user's activity pattern, that includes one or more sensors configured to be worn on a user's body and to obtain time series of measured activity parameters; a computer storage configured to store activity data; a computer processor configured to automatically determine locations of the one or more sensors on the user's body, wherein the computer processor is configured to automatically segment the time series of measured activity parameters into two or more activity periods, to determine a spatial range of the movement in an activity period, and to recognize an activity in the activity period based at least in part on the measured activity parameters and the pre-stored activity data.

These and other aspects, their implementations and other features are described in detail in the drawings, the description and the claims.

BRIEF DESCRIPTION OF THE DRAWINGS

FIGS. 6A-6D illustrate a sensor compatible with the present invention. FIG. 6A: a front view; FIG. 6B: an exploded top perspective view; FIG. 6C: a right perspective view; FIG. 6D, a rear perspective view; FIG. 6E, a top view.

FIGS. 9A and 9B show activity categories in accordance with some embodiments of the present invention.

DETAILED DESCRIPTION OF THE INVENTION

In some embodiments, a wireless sensor, comprises housing for attachment to an object, including, but not limited to, a person, an animal, a bird, an aquatic organisms/water product, a plant, a building, a machine system or module, etc.; at least one motion activity detector disposed within the housing; and a processor disposed within the housing, for processing signals from the detectors to assess activity of the object and capturing raw activity data from the detectors for further activity pattern recognition purpose.

A wearable wireless sensing device can be a clip-like sensor, pin-like sensor, watch-like sensor, band-shaped sensor.

A server provides detailed activity log of an object and activity performance comparison between multiple objects via a data network, and to recognize activity patterns of an object using raw activity data from the detectors and calculated activity metrics data from a sensor;

A method recognizes activity patterns of the object based on recognition models and capturing raw activity data from the detectors and calculated activity metrics data from a sensor, wirelessly communicated from the sensor.

Sensing network to integrate a number of sensor devices at different locations, connected with blue-tooth, Wi-Fi, etc.

Database covering normal baseline, abnormal cases with different level with 24/7 Intelligent Motion Activity Recognition for different applications, which include Battery life is an important item to extend application period, even though current battery life for an ultra-low power wireless motion activity sensor can be 6 months or even 12 months. Following proposed ways could be part of solutions to extend the battery life for applications, at least as the patent claim items:

Battery lifetime can be extended by motion active recharge, remote recharge (wireless recharge), solar way recharge, make sensing device cooler, smaller.

Figure 1A:
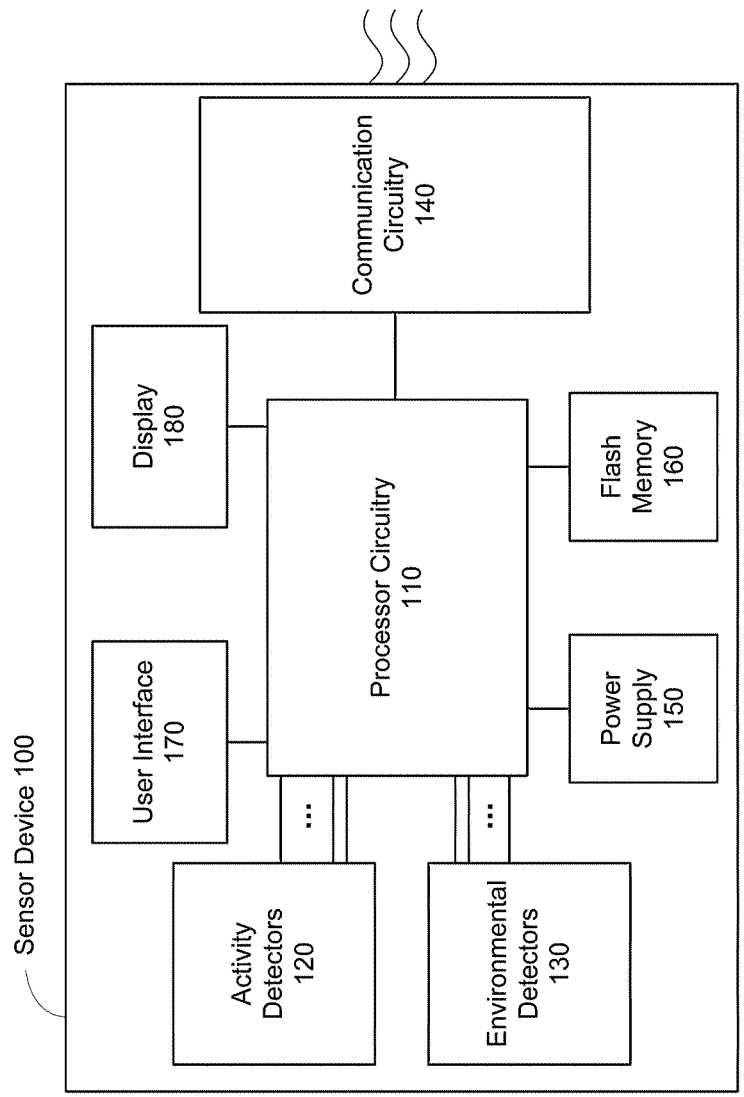
FIG. 1A illustrates a generalized block diagram of an exemplary sensor device in accordance with the present invention.

FIG. 1A illustrates a generalized diagram of a sensor device 100 for activity monitoring, and environmental information monitoring purpose. The sensor device 100 is, for example, suitable to wear around the body of the object (human being; pets, including but not limited to dog, cat, etc.; livestock, including but not limited to swine, cattle, etc.). The sensor device, as part of activity monitoring system, has raw data capturing capability for remote activity pattern recognition purpose, and dynamic configuration capability for sensor intelligence and ultra-low power purpose.

The sensor device 100 includes a processor circuitry 110 that controls the overall operation of the sensor device 100. The sensor device 100 also includes activity detectors 120 that measure various activity signals and convert them to electrical signals. The processor circuitry 110 may process resulting electrical signals and determine metrics associated with the object. The sensor 100 further includes a flash memory 160 as the storage media to save the calculated activity data and environmental data. For activity pattern recognition purpose, raw data from activity detectors may also be captured and stored in flash memory 160. The sensor device 100 also includes a communication circuitry 140 to transmit activity data and sensor status information to computing device 210, and a server 250, and receive dynamic configurations from the dynamic configuration module in the server 250.

The sensor device 100 includes a dynamic configuration module 260 which can make the sensor device 100 to be highly configurable and ultra-low power consuming. In the regard of configuration, the sensor device 100 can be highly adaptive to object's activity pattern. In default, the sensor device 100 senses, calculates, captures, records detectors data based on pre-defined object configuration 270 and sensor configuration 280, and sends detector data, raw or processed, to the remote server 250. Based on the learning result of object's activity pattern by the remote server 250, the sensor device 100 receives dynamically optimized configuration parameters in the dynamic configuration module 260 from the server 250. In the regard of ultra-low power, the sensor device 100 can be designed to achieve ultra-low power capability when the power supply 150 is powered by a battery. In default, the sensor device 100 includes a communication circuitry 140 to transmit detector data and sensor status information to the server 250. Based on the learning result of detector data and sensor status information from by the remote server 250, the sensor device 100 receives dynamically power-optimized parameters in the dynamic configuration module 260 from the remote server 250.

The sensor device 100 includes flash memory circuitry 160 for saving various data and/or firmware program. In the regard of various data saved on the flash memory 160, it includes calculated detector data which is collected by the detector circuitry 120/130, processed by the process circuitry 110 and/or transmitted to remote server 250. The flash memory circuitry 160 can also save raw activity data collected by the detector circuitry 120, and/or transmitted to remote server 250 for activity pattern recognition purpose. The flash memory circuitry 160 can also record dynamic configurations in the dynamic configuration module 260 which can be updated dynamically by the remote server 250. Notably, the flash memory circuitry 160 can be implemented either in a format of discrete chip, or an integrated block in the same package of the processor circuitry 110. The flash memory circuitry 160 is even replaceable by any non-volatile data storage device in other format that can fulfill the task mentioned above.

Furthermore, the sensor device 100 includes a power supply 150 which can be either rechargeable battery or replaceable standard battery, for portable low-power application.

Figure 1B:
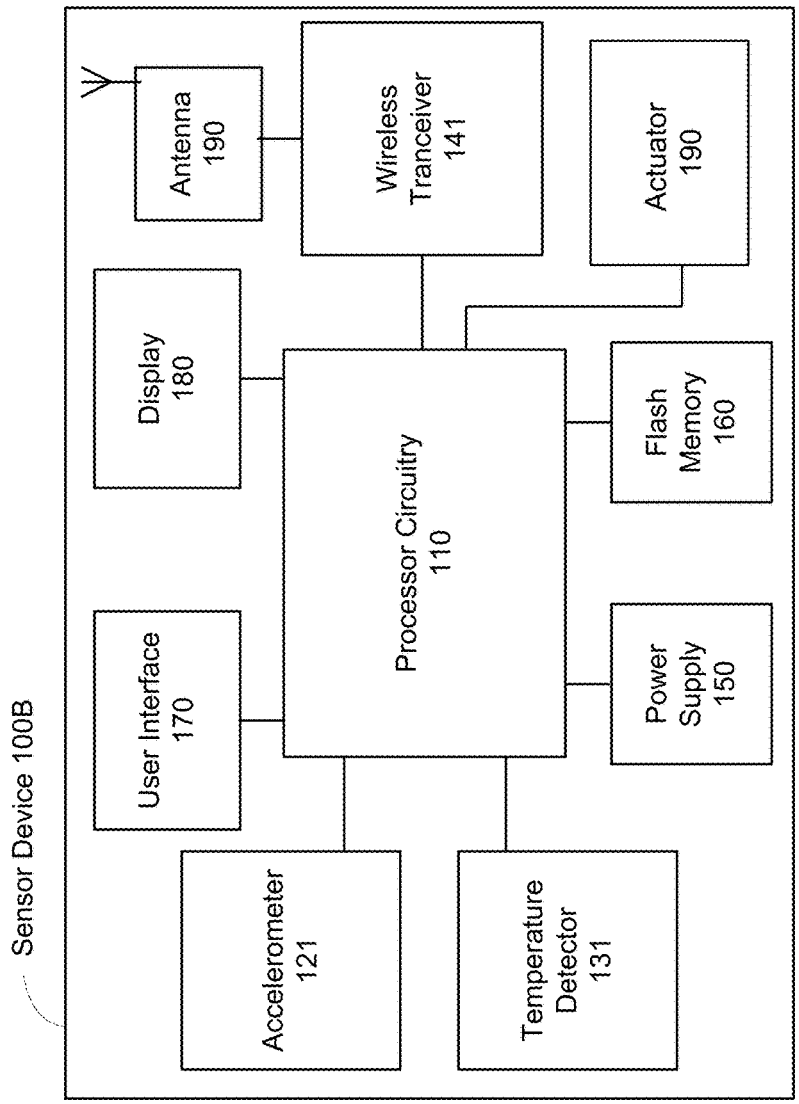
FIG. 1B illustrates an exemplary sensor device in accordance with the present invention.

FIG. 1B shows a sensor device 100B with an accelerometer 121 as the only activity detector 120, a temperature detector 131 as an environmental detector 130, and wireless transceiver 141 as communication circuitry 140. The acceleration data from accelerometer 121 alone, provides captured raw activity data 310 for activity pattern recognition by remote server 250, and calculated detector data 320 processed by processor circuitry 110. The sensor device 100B also includes one or more actuators 180. Exemplified functions of actuators can include emitting a sound or a light, producing vibrations, producing heat, ejecting a fluid (such as chemical or medicine), etc.

As for low power procedure, in this embodiment, the accelerometer 121 monitors the activity of the object who wear the sensor device 100 and can trigger an interrupt signal to wake up processor circuitry 110 when it detects the activity level is above a configurable threshold value (activity threshold) which indicates certain level of activity being undertaken. When the accelerometer 121 determines that there is no activity, the sensor device 100 can enter a low power mode (i.e., sleep or deep sleep) after a configurable interval (napping interval) automatically.

The sensor device 100 can also have power-related configurations in the dynamic configuration module 260 to minimize the power consumption. In default, the transceiver circuitry 141 of the sensor device 100 establishes the communication link to transmit activity data and sensor status information to the server 250 based on a default configurable transmit interval parameter (e.g. transmit interval) in transceiver settings 282 of sensor configuration 280. Based on the learning result of object's life style pattern, such as time slots in which success rate of communication link are the highest, object categories (human being, pets, or livestock), from the system 200, the sensor device 100 receives dynamically optimized configuration parameter (e.g. transmit interval) in transceiver settings 282 from the server 250.

Figure 1C:
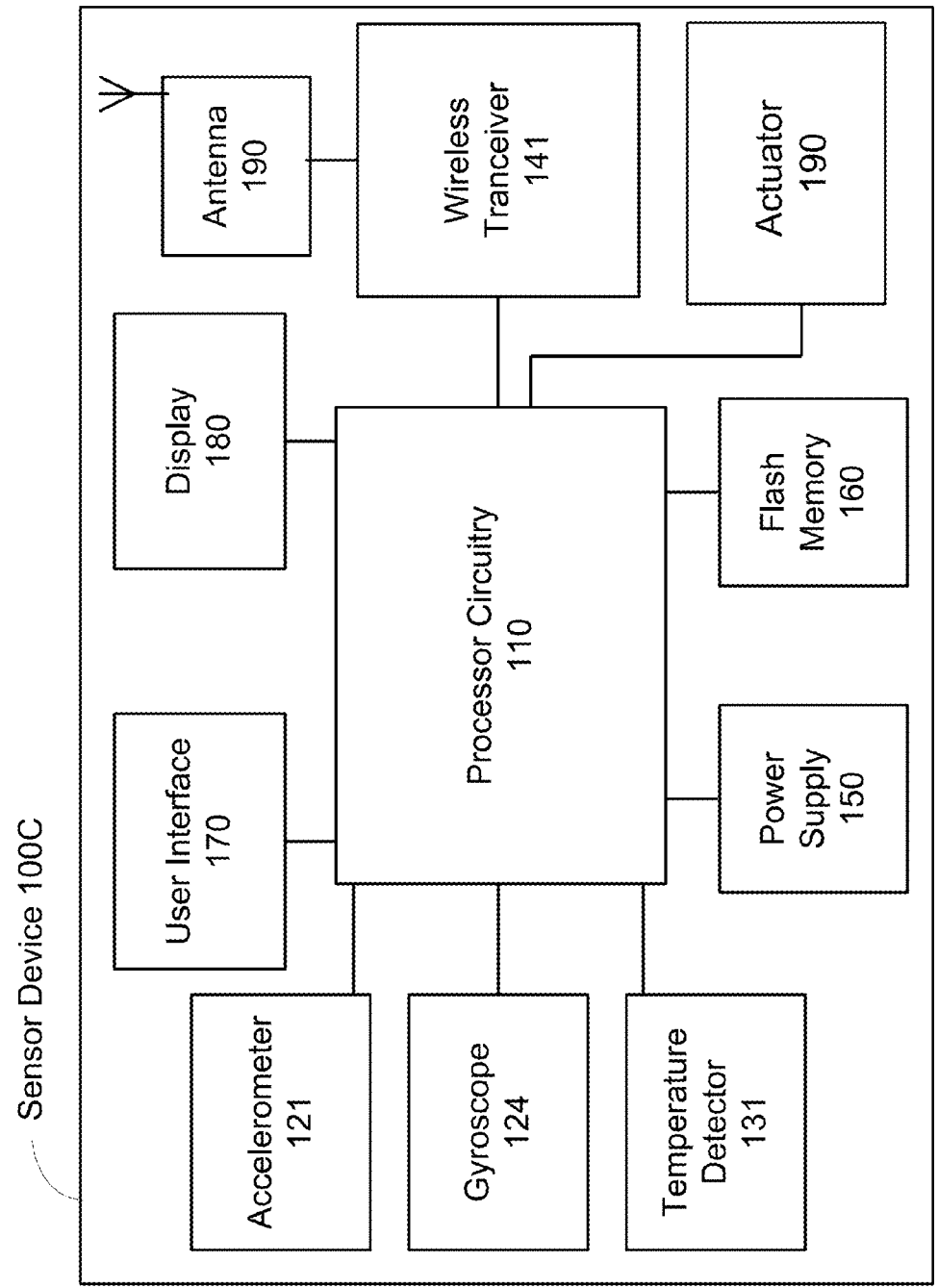
FIG. 1C illustrates another exemplary sensor device in accordance with the present invention.

FIG. 1C shows a sensor device 100C, with both an accelerometer 121 and a gyroscope 124 as multiple activity detectors 120, and a temperature detector 131 as environmental detector 130. The acceleration data from accelerometer 121, together with angular data from gyroscope 124, provides captured raw activity data 310 (shown in FIG. 9B below) for activity pattern recognition by remote server 250, and calculated detector data 320 (shown in FIG. 10 below) processed by processor circuitry 110. The sensor device 100C also includes one or more actuators 190. Exemplified functions of actuators can include emitting a sound or a light, producing vibrations, producing heat, ejecting a fluid (such as chemical or medicine), etc.

Figure 2:
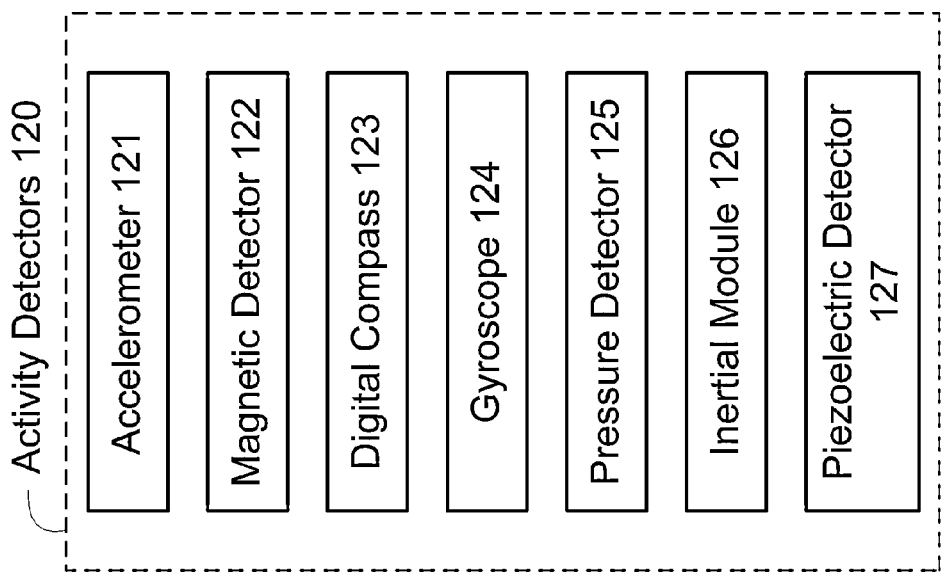
FIG. 2 is an exemplary block diagram of activity detectors suitable for the disclosed sensor device.

FIG. 2 shows an exemplary block diagram of activity detectors which include, for example, one or more accelerometers 121, magnetic detectors 122, digital compasses 123, gyroscopes 124, pressure detector 125, inertial module 126, piezoelectric detector 127 and/or other unlisted activity detectors to sense, capture, calculate and record activity data of the object. Different combinations of these activity detectors may be incorporated in the sensor devices 100. Even more, all types of detectors, whether listed or unlisted here, that generate data which is representative of the activity of the object, are intended to fall within the scope of the present inventions.

In the disclosed sensor device, 9 degrees of freedoms can be measured by the accelerometer 121, the gyroscope 124, and a magnetometer (e.g. the magnetic detector 122). The activity sensors 120 can also include an altimeter that measures height from the sea level, a GPS measurement device that measure positions of the sensor device on earth surface.

Figures 3, 4:
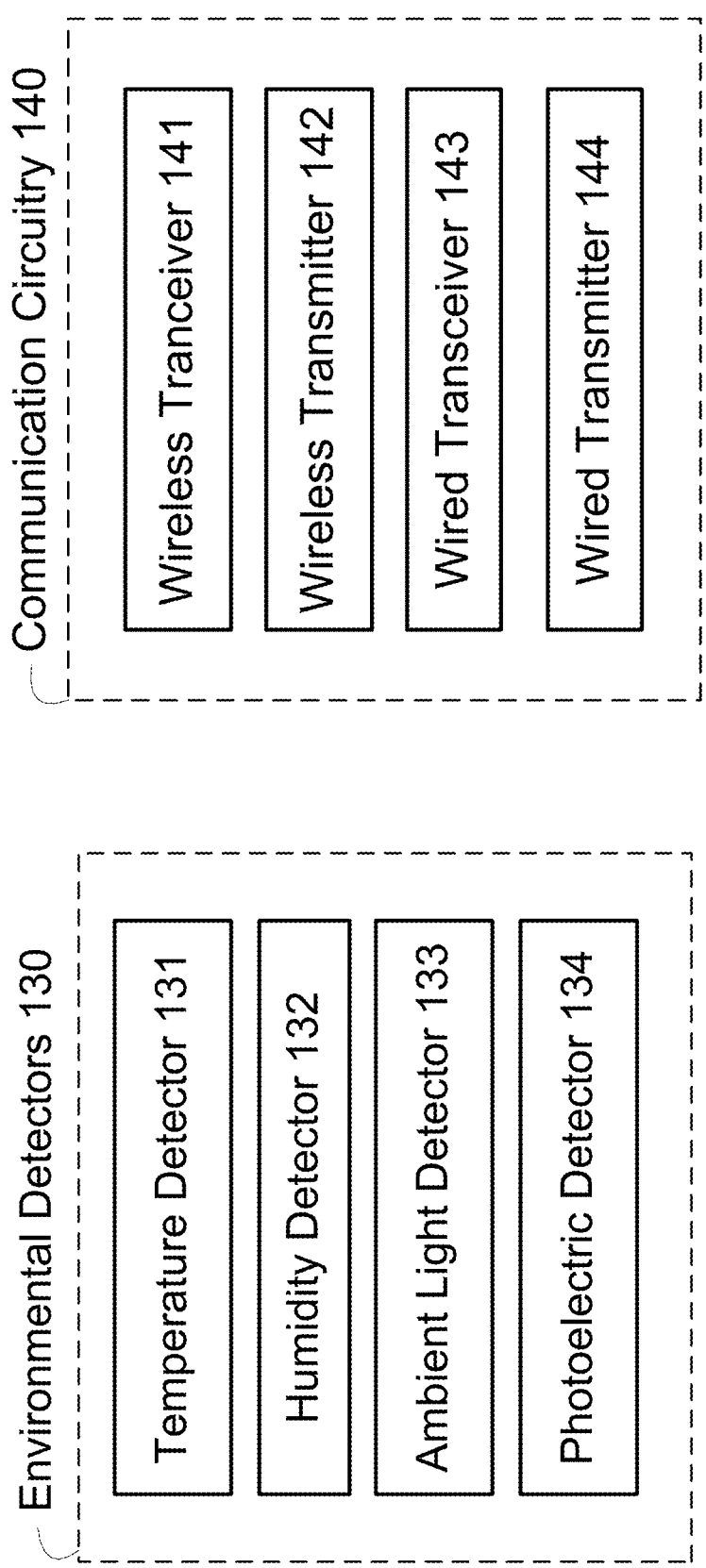
FIG. 3 is a block diagram of exemplary environmental detectors suitable for the disclosed the sensor device.
FIG. 4 illustrates a block diagram of an exemplary communication circuitry configured to establish the communication link between the sensor device and the computing device.

FIG. 3 shows a block diagram of the environmental detectors 130, which may include a temperature detector 131, humidity detector 132, ambient light detector 133, and/or photoelectric detector 134. The environmental detectors may also employ any known or unknown detectors to provide environmental data which is representative of environmental condition of the object.

FIG. 4 shows an exemplary communication circuitry 140 that reflect different data transfer methods to build the communication link 230 between the sensor device 100 and the computing device 210. Communication link 230 can be, but is not limited to, any known wired connection, including but not limited to electronic data link, fire wire, a network cable connection, a serial connection, a parallel connection, USB, or any known wireless data connection, including but not limited to Bluetooth, Bluetooth Low Energy, WLAN, ANT, and proprietary link protocol. Depending upon the implementation, the communication link 230 may employ various communication circuitries 140, operating in one or more modes of transmission and/or receiving. For example, the communication circuitry 140 may include wired transceiver 141, wireless transceiver 142, or wired transmitter 143, wireless transmitter in the case that the sensor device 100 need not receive data back from the computing device 210. The function of the communication link 230 is to transmit and receive data to and from the sensor device 100 to the remote server 250. Depending on the implementation, the communication link 230 may also be coupled to several sensor devices to provide a network of sensors all connected to the computing device 210.

Figure 5A:
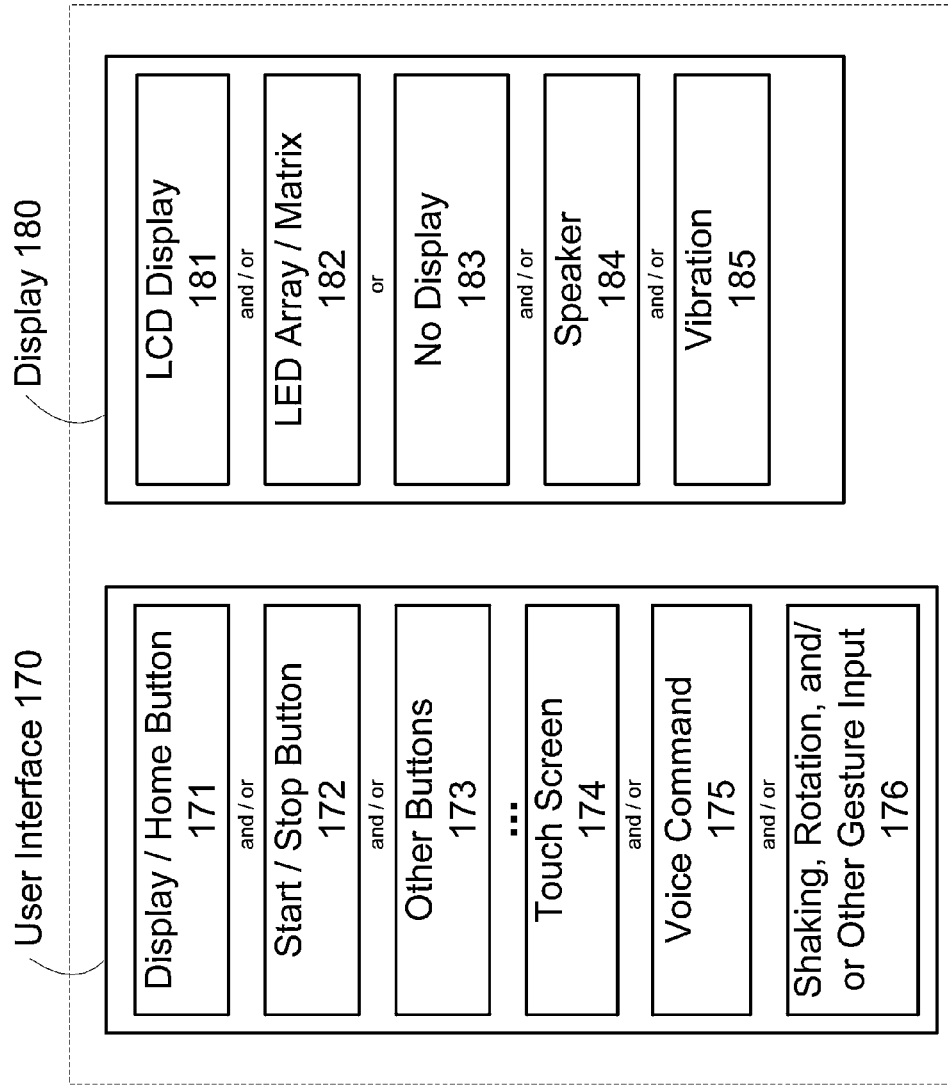
FIGS. 5A-5C show user interfaces compatible with the present invention.
Figure 5B:
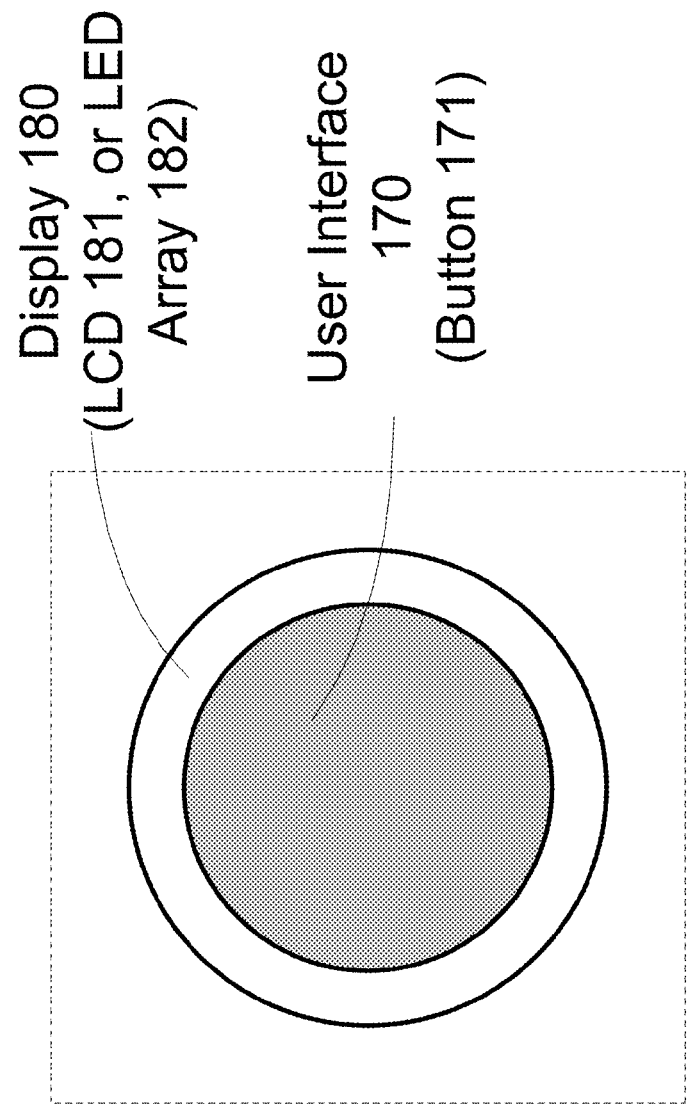
Figure 5C:
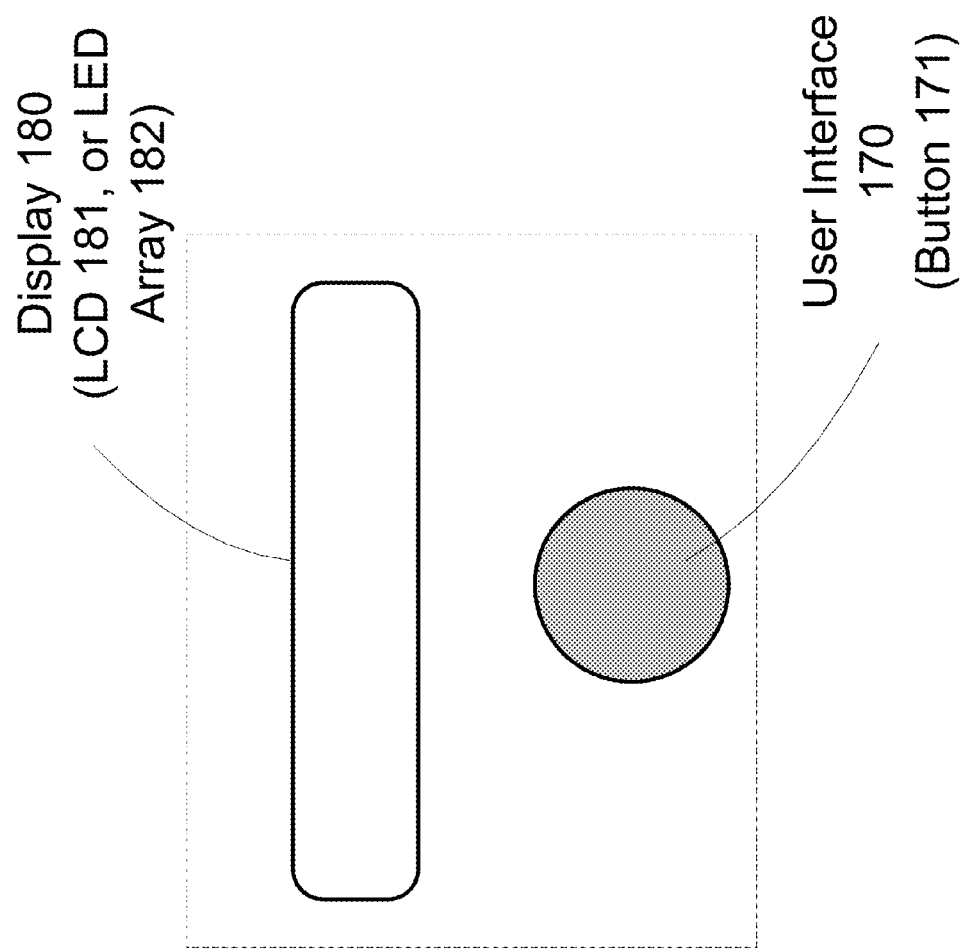

FIGS. 5A-5C show user interfaces compatible with the present invention. The disclosed portable sensor devices (e.g. 100, 100B, 100C in FIGS. 1A-1C) can include a user interface 170 and/or a display 180 to facilitate communication with the user. (for example, FIG. 1A) The user interface may include one or more buttons 171-173, voice command 175, gesture input 176 one or none of display (181-184), speaker and or microphone 184, vibramotor 185, and/or an input mechanism, for example, a touch screen 174. Indeed, any manner of or mechanism for outputting and/or inputting of data and/or commands are intended to fall within the scope of the present inventions. FIGS. 5B-5C are two illustrative examples of such user interfaces and displays.

FIGS. 6A-6E illustrate an exemplified sensor device 600 compatible with the present invention. The sensor 600 includes a clip that allows it to be easily attached to a user's body. It monitors wearer's daily energy expenditure, sleep quality, postures, dangerous events such as fall-down of elderly people, etc. The sensor device 600 can be connected to a smart device wirelessly such as a smart phone, or to a personal computer wirelessly via a dedicated base station (not shown) for data communication.

Figure 7:
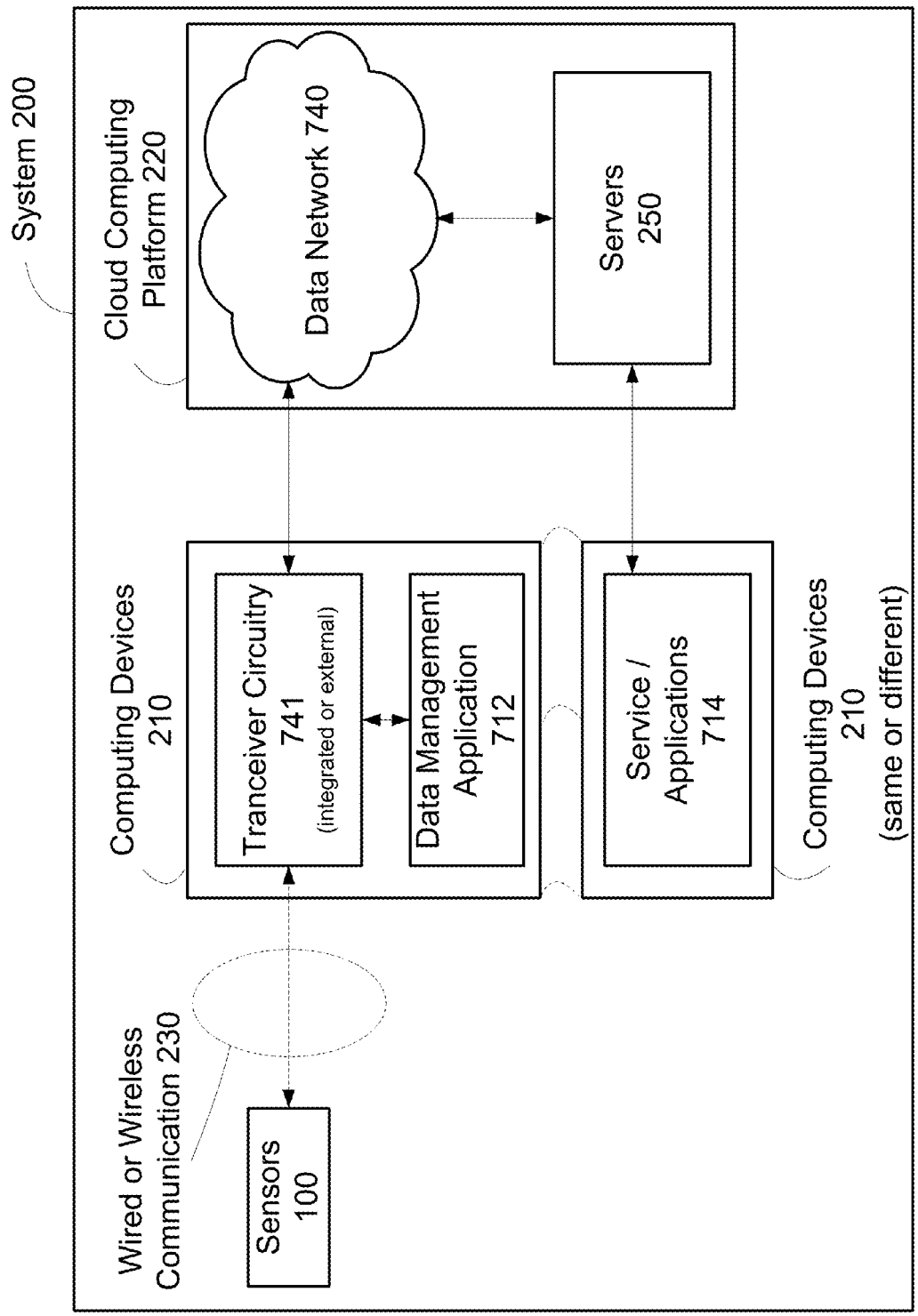
FIG. 7 is a block diagram for a system having various functions including activity log and performance comparison in accordance with some embodiments of the present invention.

FIG. 7 is a system block diagram including activity log and performance. Activity data, raw or processed, which contains activity information and physiological state, together with environmental data of the object is captured and transmitted, either asynchronous or in real-time, to a remote cloud computing platform 220 including a data network 240 and one or more servers 250, where it is stored for later activity pattern recognition, and presentation to end object via remote access from the Internet. The computer device 210 includes transceiver circuit 741, data management application 712, and a service or application 714.

Figure 7A:
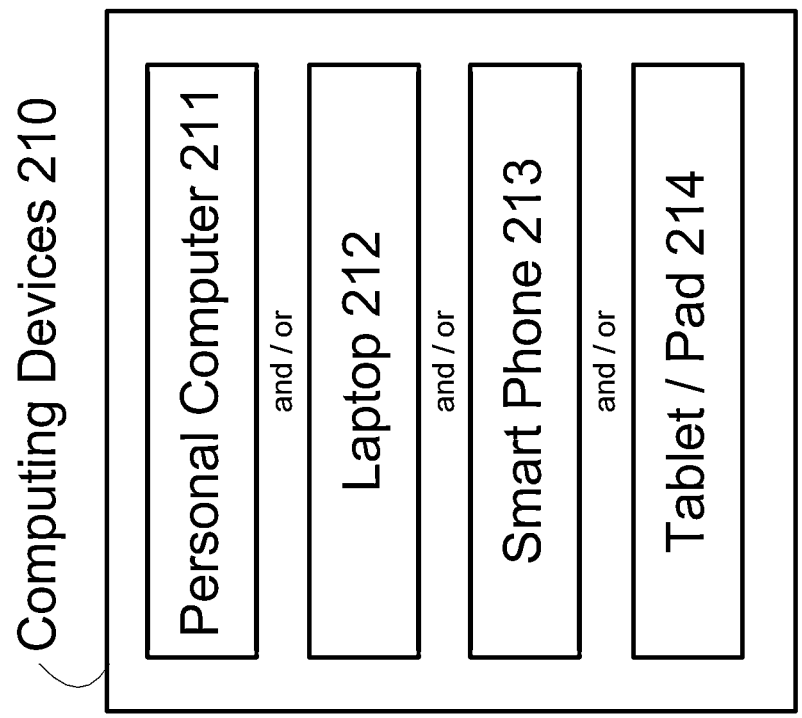
FIG. 7A shows examples of computing devices compatible with the disclosed systems and methods.

FIG. 7A shows exemplary computing devices that are connected to sensor devices and serve as computing and displaying devices for the claimed sensor system. The computing devices 210 includes, but not limited to personal computers 211, laptop 212, smart phone 213, and/or tablet computer 214.

Figure 8A:
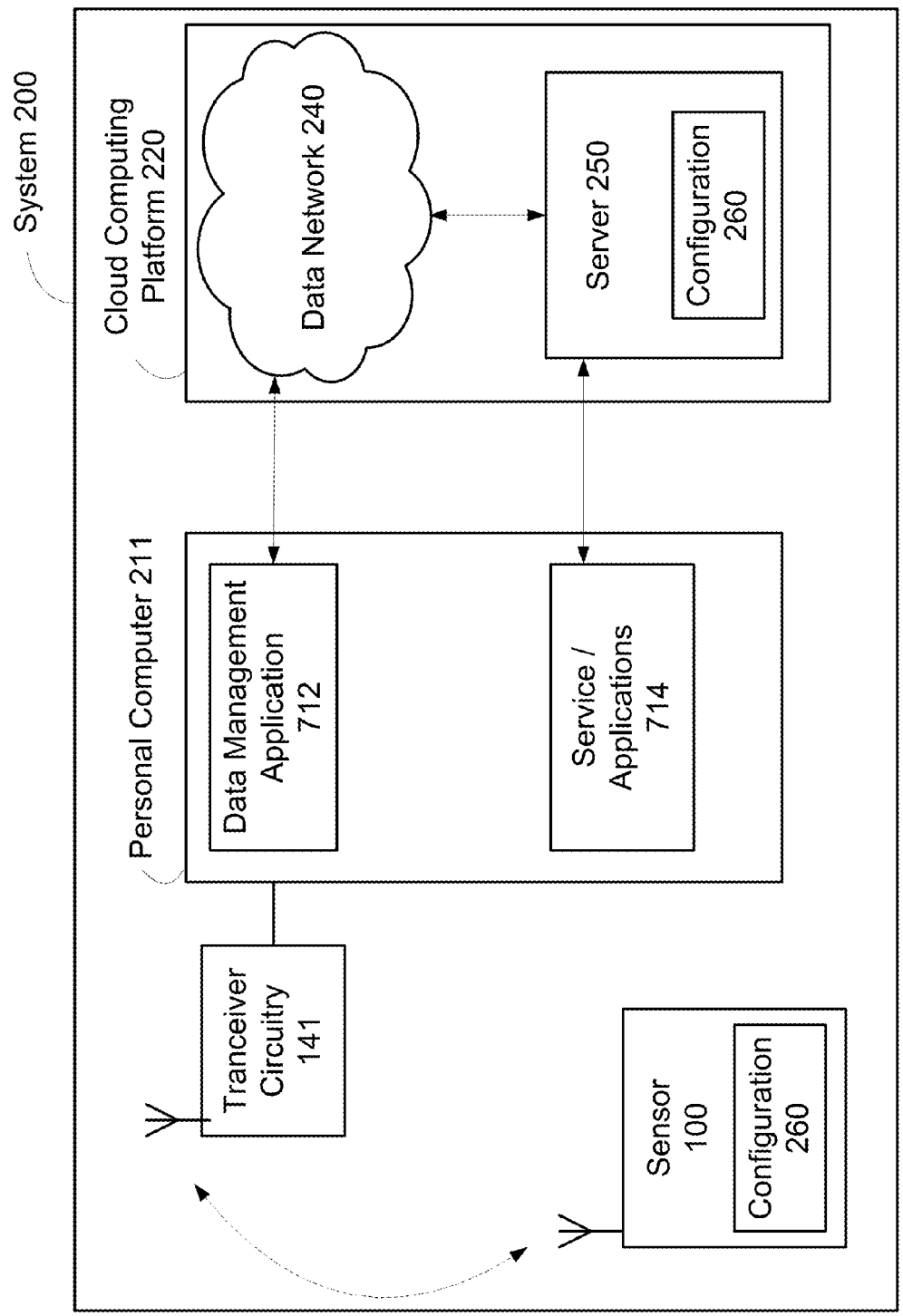
FIG. 8A is a system block diagram in accordance with some embodiments of the present invention.

FIG. 8A illustrates an exemplary wireless sensor system block diagram according to the present invention. Processed activity data, which contains activity information and physiological state, together with environmental data of the object is captured and transmitted by sensor 100, either asynchronous or in real-time, via a personal computer 211, to a remote cloud computing platform 220, and present to end object via remote access from the Internet.

Figure 8B:
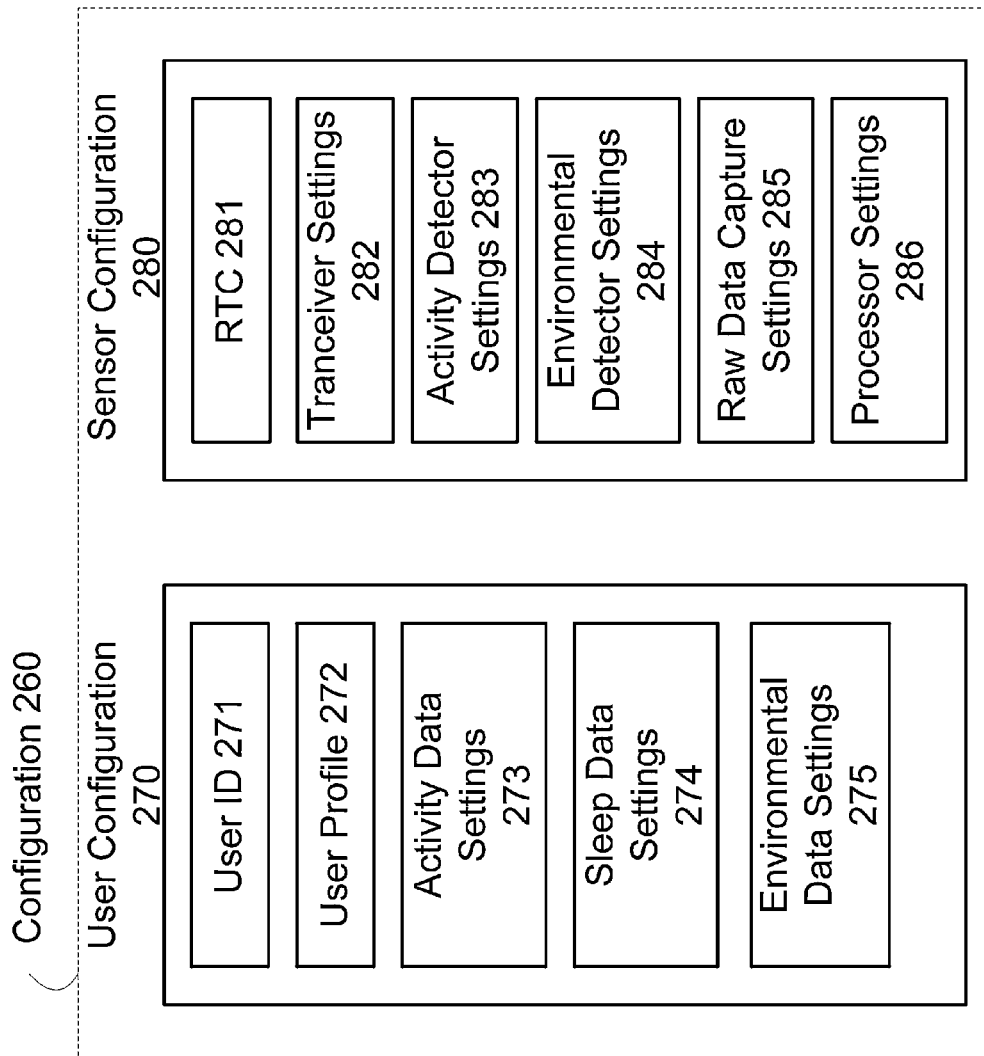
FIG. 8B is a block diagram for sensor configuration in accordance with some embodiments of the present invention.
Figure 8C:
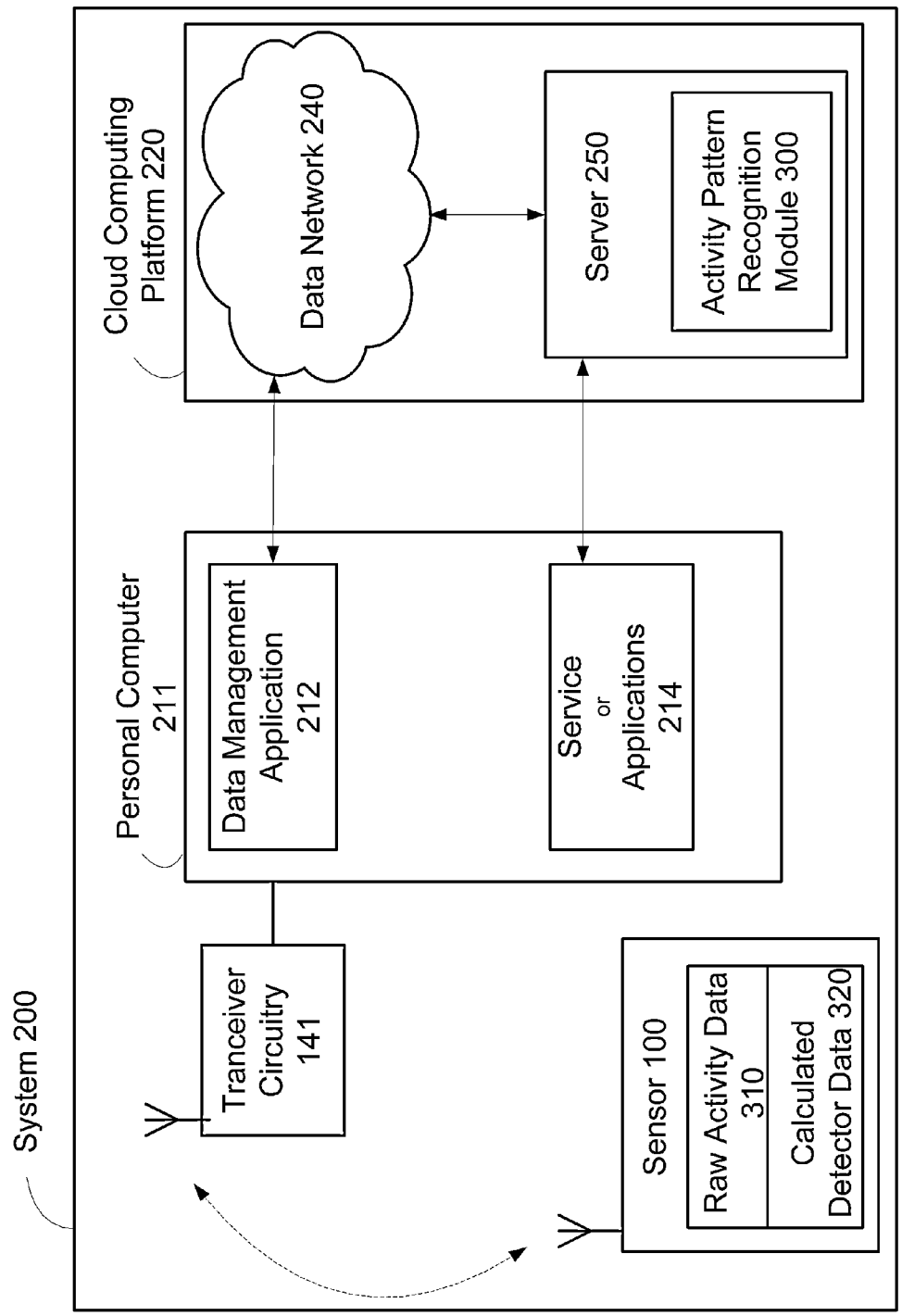
FIG. 8C is a system block diagram in accordance with some embodiments of the present invention.

FIG. 8B illustrates an exemplary wireless sensor system block diagram with activity pattern recognition capability. Activity data, raw and processed, which contains activity information and physiological state, together with environmental data of the object is captured and transmitted by sensor 100, either asynchronous or in real-time, via a personal computer 211, to a remote cloud computing platform 220, where it is stored for later activity pattern recognition, and presentation to end object via remote access from the Internet. FIG. 8C is another system block diagram in which the server 250 stores with an activity pattern recognition module 300.

FIG. 9A shows exemplary activity patterns that are recognized by sensor system. The activity patterns 330 include, but are not limited to, walking on a flat ground 331, running on flat ground 332, sitting 333, lying down 334, standing 335, hiking upwards 336, hiking downwards 337, bicycling 338, and/or other sports patterns 339.

FIG. 9B illustrates exemplary raw activity data that are processed and recognized by sensor system. The raw activity data 310 includes, but are not limited to accelerometer raw data 311, gyroscope raw data 312, magnetometer raw data 313, and/or raw data from other activity detectors 314, which are preferably processed by the remote server 250, for activity pattern recognition purpose.

Figure 10:
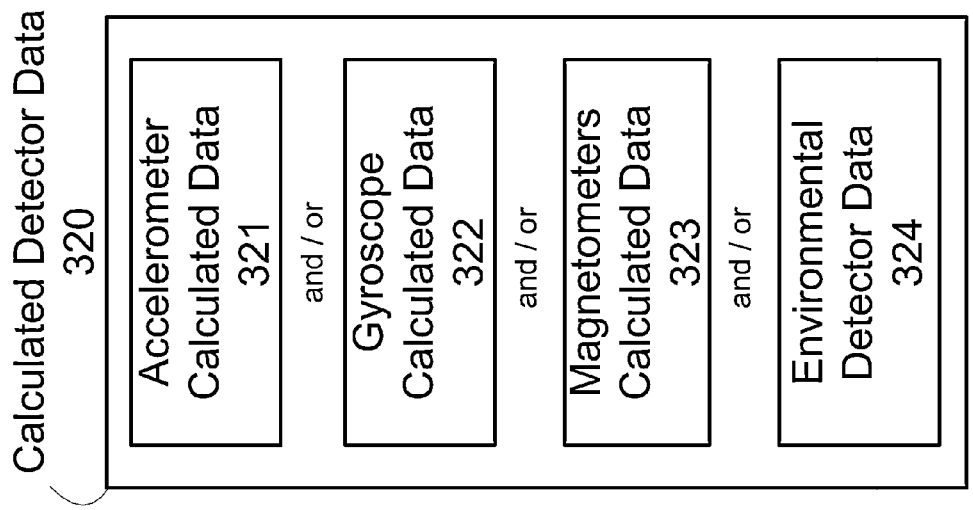
FIG. 10 show exemplified calculated data for activity pattern recognition in accordance with some embodiments of the present invention.

FIG. 10 illustrates exemplary calculated detector data that are processed by processor circuitry by sensor system. The calculated detector data 320 includes, but are not limited to accelerometer calculated data 321, gyroscope calculated data 322, magnetometer calculated data 323, and environmental detector data 324.

The sensor device 100 is adapted to couple to the body of the object. Sensor device 100 is preferably worn by an object on the body, for example as clipping in the pocket, or as necklace or part of an arm band, etc. The sensor device 100 can include one or more activity detectors, which are adapted to generate signals to capture activity characteristics of an object, and one or more environmental detectors, which are adapted to generate signals to capture environmental characteristics of an object. Activity characteristics include, but are not limited to activity parameters of an object, such as sitting/standing posture, fall down event, inactivity for a predefined period, convulsion; fitness information including but not limited to speed, velocity, angular velocity, position, displacement, distance; and/or physiological parameters, including but not limited to body temperature, heart rate, pulse rate, beat-to-beat heart variability, blood pressure, body fat, calorie, etc. Activity characteristics can also include raw activity data 310, such as accelerometer raw data 311, gyroscope raw data 312, magnetometer raw data 313, and/or raw data from other activity detectors 314, which are preferably processed by remote server 250, for activity pattern recognition purpose. Environmental characteristics include, but are not limited to, ambient temperature, humility, air quality, light intensity, water quality, sound quality, location, etc.

Notably, it is to be understood that the data indicative of the various activity characteristics and environmental characteristics is generated by the one or more sensor devices 100 without departing from the scope of the present invention.

The processing of activity data is a distributed computing process. In some embodiments, the sensor device 100 is a low-power device with limited calculation capability. The processor circuitry 110 of sensor device 100 processes low-complexity tasks, for example, monitor and calculate the activity data to detect sitting/standing postures, dangerous events including but not limited to fall-down, inactivity for a pre-defined period, convulsion monitor and calculate the activity data to derive simple activity metrics parameters such as speed, pace, calorie, distance, movement, etc. For example, the processor circuitry 110 can be programmed to calculate calorie burned or average speed during a defined period of time. The processor circuitry 110 of sensor device 100 is able to monitor and derive physiological parameters of an object, such as heart rate, body temperature, etc. The processor circuitry 110 of sensor device 100 is programmed to derive such information using well known methods based on the activity data captured by the sensor device 100.

For high-complexity tasks, including but not limited to activity pattern recognition, the processor circuitry 110 of the sensor device 100 can capture raw activity data 310 and transmit to the remote server 250 when communication link between the sensor device 110 and the remote server 250 is available. The remote server 250, which has powerful processing capability, of not only remote computing devices but also processing algorithms, can take the raw activity data 310 as input, with or without the calculated detector data from sensor device 100 as auxiliary input, output results of complex tasks, including but not limited to activity patterns 330 of an object. The activity patterns 330 include, but are not limited to, walking on the ground 331, running on the ground 332, sitting 333, lying down 334, standing 335, hiking upwards 336, hiking downwards 337, bicycling 338, and/or other sports patterns 339.

Figure 11:
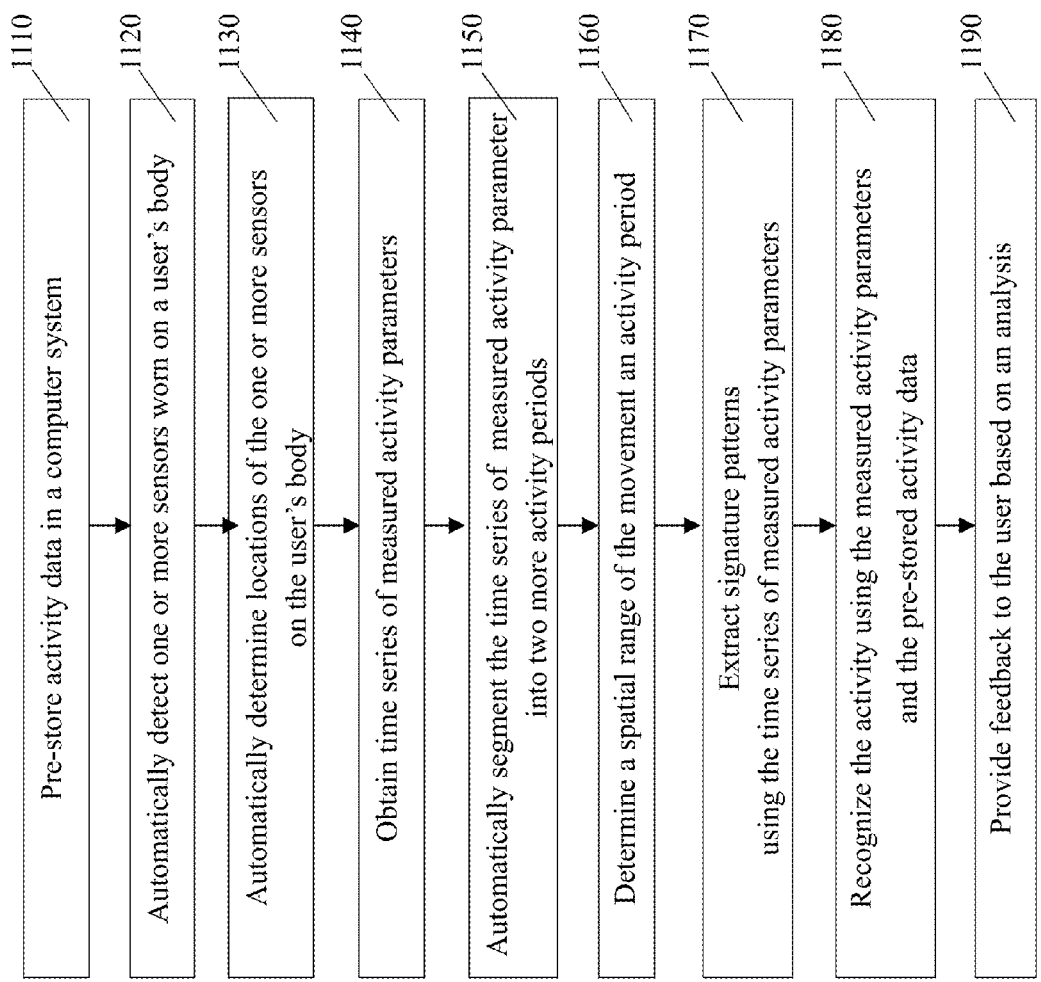
FIG. 11 is a flowchart of automatically detecting activity pattern in accordance with some embodiments of the present invention.

The disclosed system and methods can automatically detect daily activities such as walking and various sports activities. Referring to FIG. 11, activity data is pre-stored in a computer system such as the computing devices (e.g. 210 in FIGS. 7 and 7A) or a cloud computing system (e.g. 220 in FIG. 7) (step 1110). The activity data can cover movement such as walking, running, stair climbing, mountain climbing, hiking, driving, taking elevator, dancing, playing soccer, basketball, tennis or ping pong, etc., different styles of swimming, diving, sleeping, sitting, driving/in transportation, jumping, rotating, etc., and dangerous activities shaking, falling down, and bad posture. For pets and livestock, the activities can include but not limited to: walking, wandering, running, lying down, flying, rotating, shaking, diving, climbing, etc.

Specifically, the activity data can include spatial distributions of speed or velocities, including angular velocities. The spatial distributions can be in three, two, or one dimensions.

The activity data can capture absolute geo locations, relative positions, altitude (or height), speeds, velocities (in three directions), rotations (around one, two, or more axes), etc.

In some embodiments, the pre-stored activity data specify the locations of the sensors on the wearing user's body. The speeds, velocities, and angular velocities in many activities are dependent on which part of the body the sensors are placed on the user's body (e.g. wrist, arm, waist, ankle, etc.).

In some embodiments, the pre-stored activity data can include signature patterns that exist in common activities, including personalized signature pattern in a particular user's activity. Signature patterns can exist in distributions, rhythms, postures, and secondary parameters can be calculated from the time series of the measured parameters.

In some embodiments, the pre-stored activity data can include personalized data specific to a user. In particular, the signature pattern can be personalized and specific to the user's behavior in the activity. For example, even if the size of the ping pong table is standard, different users can still play ping pong in different styles. The speed and velocity distributions over the field around a ping pong table can be recorded specific to a user.

In some embodiments, the activity data can include Euler angles, Quaternion angles, waveform, frequencies or rhythms, and patterns extracted from the user's movements. In particular, the sensor devices can reveal a user's body posture at each time. The user's posture can be compared to the movement speeds at different time points.

When one or more sensors (e.g. 600 in FIG. 6A-6E) are placed on a user (a person, a pet, etc.), the one or more sensors are automatically detected (step 1120) by pattern recognition technology. Firstly, the sensor device automatically distinguishes the Detached Mode (not attached to body) from the Attached Mode of sensor device by observing the signal pattern of the sensor device over a pre-defined period of time. The one or more sensors can be placed on the user's skin or on his or her clothing.

Importantly, the locations of the sensors are determined (step 1130). The locations of the sensors on the user's body is important because the movement patterns and velocities of the sensors are dependent on the where they are on the user's body. For example, when a user plays table tennis, the movement and velocities of the sensors are different if they are placed on the wrist, the arm, or the waist of the user. Two different approaches are claimed to determine the location of the sensor device on body. In some embodiments, the sensor devices utilize pattern recognition method to determine the location of the sensor devices around the body. The sensor device records activity information mentioned above when the wearer is in stable activity mode (such as walking, running, still, etc.) which can be easily recognized. In such stable activity mode, Euler angles or Quaternion angles of the sensor device are calculated. The location information of the sensor device around the body can be derived from the Quaternion angles. In some embodiments, the sensor devices utilize modularization hardware design technology which includes a stand-alone module and detachable accessories (in the form of wristband, clip, case, etc.). The stand-alone module has a detection circuitry and a hardware interface to interact with accessories. The detachable accessories have different digital signature circuitries (for example, resistance, capacitance, inductance, impedance) to present different signal patterns (in the form of voltage, current, etc.) to distinguish themselves from each other.

Once worn by the user, the one or more sensors can continuously send data of measured activity parameters to the computer system (e.g. the computing device or the cloud computing system). Time series of measured activity parameters are obtained and recorded by the sensor device and the computer system (step 1140). The measured activity parameters can be referred to as raw activity data, as described above. The measured activity parameters can include the different movement parameters such as positions, displacements, distances, speeds, angular velocities, altitude, etc., physiological parameters such as body temperature, heart rate, pulse rate, beat-to-beat heart variability, blood pressure, body fat, calorie, etc., and environmental characteristics such as ambient temperature, humility, air quality, light intensity, water quality, sound quality, location, etc.

The disclosed computer system can automatically detect a period of inactivity or slow activity (idle period) in between more active periods of movements (walking, running, playing sports). In some embodiments, the disclosed computer system can use the ratio of average speeds as a measure to segment periods of inactivity and activity, or between different active periods. The speeds can be measured over linear movements or rotational movements. For example, the ratio of average speeds can be predetermined as 2 or above for particular user, or as 3 or above for another user. Average speeds in small time intervals (e.g. each minute) can be computed and compared. When two extended periods of time have a ratio of average speeds higher than the predetermined threshold (e.g. 2 or 3), the disclosed system can automatically segment the time series of measured activity parameter into different activity periods (step 1150) to conduct more detailed analysis of the movement patterns (spatial and temporal).

Similarly, in some embodiments, the disclosed computer system can use the ratio of average accelerations as a measure to segment periods of inactivity and activity, or between different active periods. For example, the ratio of average acceleration can be predetermined as 2 or above for particular user, or as 3 or above for another user. When two extended periods of time have a ratio of average accelerations higher than the predetermined threshold (e.g. 2 or 3), the disclosed system can automatically segment the time series of measured activity parameter into different activity periods (step 1150) to conduct more detailed analysis of the movement patterns (spatial and temporal).

The spatial range of the movements in the activity period is determined (step 1160) by the sensor device or the computer system. For example, a user that plays tennis, his or her movements are defined by the dimensions of half of a tennis court (39 ft. by 27 ft. or 36 ft. for single and double respectively) during one game. Different tennis games can be separated by a low activity period and are often segmented to be different active periods. In table tennis, the player move around a ping pong table that is 274 cm by 152.5 cm, and 76 cm in height. A badminton court, on the other hand, is smaller than a tennis court, but much larger than player's movement range around a ping pong table. For different sports, the height of user's body can also vary because some sports involve more jumping and hand-raising (e.g. basketball and volleyball) than others (running).

Next, signature patterns are extracted in the time series of measured activity parameters (step 1170). Distributions, rhythms, postures, and secondary parameters can be calculated from the time series of the measured parameters (i.e. the calculated detector data 320 in FIGS. 1B, 1C, 8C, and 10). The secondary parameters can include angular velocity which can be calculated from change in velocities over time. The rotation of a user's body can also be derived using time series of velocities at different parts of the user's body. In another example, postures of a user can be determined by measuring positions of several parts of a user's body. The repeatable patterns, frequencies, and rhythms in positions, height, speed, and velocities represent signature patterns, which can be compared to the pre-stored signature patterns in the computer system. A matching of pre-stored signature patterns for known activities can lead to positive identification of one or more activities in the activity period.

The activity is then recognized using the measured data and the pre-stored activity data (step 1180) using for example activity pattern recognition module (e.g. 300 in FIG. 8C). First, the above determined spatial ranges (in longitude, latitude and altitude or height) give a clue on the type of activities that the user is engaged in the active period. For example, running on a flat ground or on treadmill, hiking, mountain climbing, soccer, basketball, tennis, table tennis, sitting on a chair, working in a kitchen, etc. all have different spatial ranges. The measured spatial ranges can compared with the spatial ranges for different activities pre-stored in the computer system. It should be noted that some spatial ranges may be specific to a user. For example, the movement rage when a user cooks in a kitchen is dependent on the size and the layout of his/her kitchen.

Secondly, the amplitude and patterns in speeds, velocities, and angular velocities usually differ for different activities. For example, different swimming styles such as backstroke, breast stroke, butterfly, and free style all have their different rhythms and movement patterns. Moreover, even for the same swimming style, different swimmers can exhibit different movement patterns. Some of these patterns can already be pre-stored in the computer system, which can be used to compare and aid the recognition of the particular activity that the user is involved in.

Furthermore, the activity patterns can be recognized using linear or non-linear algorithms, including but not limited to, artificial neural networks, decision trees, memory-based methods, statistical filtering, multi-linear regression, locally weighted regression, decision trees, artificial neural networks, stochastic search methods, classification techniques, k-means classifiers, and decision trees, can be employed to map the activity data from the sensor devices (e.g. 100, 100B, 100C in FIGS. 1A-1C) to a preferable activity pattern 330 (FIG. 9A).

The recognition of patterns in the activity data can include training and prediction. First, training data set is collected when subjects wearing sensor device 100 are in specific activity pattern, including but not limited to sitting, hiking upwards, or gesturing, etc. As the collected training data set, raw activity data from sensor device 100, known activity pattern, and/or sensor device, location on the body, can be used as inputs to the algorithm development process. Notably, the training data set can also include raw activity data, and/or the corresponding activity pattern that the object manually inputs.

Second, a prediction model, which is built on the training set and capable to map the training set to the corresponding activity pattern, is used to predict the test set, which represents the untested raw activity data collected from the object. At this stage, the sensor device captures raw activity data 310 of the object based on a defined time interval and/or activity intensity threshold and transmit to the server 250. Based on the raw activity data, the prediction model makes predictions on activity patterns of the object. It is to be understood this pattern recognition invention can be used in a method for doing interactive gaming or sporting for real-time operation, or daily activity logging for asynchronous operation.

Still referring to FIG. 11, the user's movement patterns (speed, locus), etc. and postures can be analyzed. Feedback can be provided to the user based on the analysis (step 1190). In some embodiments, the feedback can be implemented by sending control data from the computer system to the sensor, which can control the actuator 190 (FIGS. 1B and 1C) to produce sound, music, voice, light, vibrations, heat, etc., which can guide the user to adjust his or her movements.

In the regard of remote computing devices, stand-alone server or resizable computing servers, such as Amazon Elastic Compute Cloud (Amazon EC2) can be employed as remote computing devices for high-complexity tasks.

These traditional techniques or methods can be implemented in the present inventions or modified to adapt to the invention. It is to be understood that these embodiments of the inventions are only exemplary and are not intended to be exhaustive or limiting of the inventions to, for example, the precise forms, techniques, flow, and/or configurations disclosed.

In some embodiments, the system 200 includes the dynamic configuration module 260 in the remote server 250 and the sensor device 100, which can make the sensor device 100 to be highly configurable and ultra-low power consuming. In the regard of configuration, the sensor device 100 can be highly configurable and manipulatable by the server 250. In default, the sensor device 100 senses, calculates, captures, records detectors data based on pre-defined object configuration 270 and sensor configuration 280, and sends detector data, raw or processed, to the remote server 250 based on pre-defined transceiver configuration setting 282. Based on the requirements the system 200 targets, the sensor device 100 receives dynamically optimized configuration parameters in the dynamic configuration module 260 from the server 250 and adjusts the program accordingly. In an exemplary embodiment, by updating the transceiver setting 282 of the sensor device 100 within the network, the server 250 can change the transceiver of the sensor device 100 from asynchronous communication mode to real-time communication mode, for real-time measurement and/or activity detection purpose. Moreover, the server 250 can remotely update Real Time Clock (RTC) 281, transceiver settings 282, including transceiver mode, transmit interval, transmit power level, receive interval, duration, activity detector settings 283, including activity detector enable parameter to enable specific activity detector, activity tracking interval, activity level threshold to determine activity intensity, environmental detector setting 284, including environmental detector enable parameter to enable specific environmental detector, environment monitoring interval, raw data capturing settings 285, including raw data enable parameter to enable raw data capture functionality, raw data interval to specify the interval to capture raw data, raw data size to specify the size of each raw data sample, processor circuitry settings 286, such as deep sleep interval to define the interval before entering deep sleep mode.

In the regard of ultra-low power, the dynamic configuration module 260 in the remote server 250 and the sensor device 100 can be used to make the sensor device in ultra-low power operation mode. In an exemplary embodiment, in default, the sensor device 100 includes a wireless transceiver circuitry 181 which is the most power consuming block in sensor device 100. Based on the learning result, such as communication link success rate between the sensor device 100 and the transceiver circuitry 181 on computing device 210 and sensor status information, the remote server 250 updates transceiver setting 282, such as transmit interval or schedule of the sensor device dynamically.

This disclosed systems and methods can also be used in, but not limited to, one or more of the following applications:

Family and Healthcare Applications

For children to prevent abnormal bone growth: when a child sits down, turning on the sensor monitoring function to monitor his/her sitting posture, a sensor is able to sense a body sitting angle difference larger than 3 degree, to release alarm to a child or his/her teacher or parent, then to take corrective action.

For office workers to chronic discomfort which is typical ergonomic issue for offer worker sitting down for a long time to work. A sensor is able to sense a body sitting angle difference larger than 3 degree, to release alarm to an office worker, his/her colleague, relative, or family member, then to take corrective action.

Military training for soldier to monitor his/her body posture when he/she stands or sits.

Elderly or a Patient Fall & Danger Monitoring & Alarming

Fall down monitoring for an elder or a patient, a sensor is able to monitor fall down such sudden motion activity, and to send alarm signal promptly through one of wireless ways to a nurse, elder or patient family member to take action to minimize further damage, and to carry out necessary medical treatment.

To monitor no motion activity for a predefined period for an elder or a patient, who may be temporally loss consciousness on a bed or a chair, in this way, taking action promptly could save life.

To monitor convulsion for an elder or a patient and send alarm signal promptly through one of wireless ways to a nurse, elder or patient family member to promptly take action to carry out necessary medical treatment.

Baby and Child Monitoring in a Family, a Kindergarten, a Resort Center, Etc.

Baby monitoring when a baby is on bed, to prevent a baby from falling to the ground, one can arrange a baby motion activity range limit area in a wireless sensor which is worn on the baby, when the baby moves beyond the critical motion activity range boundary, a sensor would send an alarming single to an adult, such as a babysitter, etc.

Children care for a kindergarten playground yard or a resort center, one can arrange a child motion activity range limit area in a wireless sensor which is worn on the child, when the child moves beyond the critical motion activity range boundary, a sensor would send an alarming signal to an adult, such as a kindergartner teacher, a babysitter, etc.

Alzheimer's Disease (AD) Patent Monitoring

One can arrange an AD patient motion activity range limit area in a wireless sensor which is worn on an AD patient, when an AD patient closes to the critical motion activity range boundary, a sensor would send an alarming signal to AD patient family member, a nurse, AD patient living building service people, etc. to prevent AD patient from wandering to get lost.

Parkinson Disease Patient Monitoring

Fall down monitoring for a Parkinson disease patient, a sensor is able to monitor fall down such sudden motion activity, and to send alarm signal promptly through one of wireless ways to a nurse, Parkinson disease patient family member to take action to minimize further damage, and to carry out necessary medical treatment To monitor no motion activity for a predefined time for a Parkinson disease patient, who may be temporally lose consciousness on a bed or a chair, in this way, taking action promptly could save life.

Pet Motion Activity Monitoring

One can arrange a pet motion activity range limit area in a wireless sensor which is worn on a pet, when a pet moves beyond the critical motion activity range boundary; a sensor would send an alarming single to the owner of the pet, a pet care service people, etc. to prevent a pet from going out to get lost.

Fitness Tracking

Daily energy expenditure monitoring for a wearer, an attached sensor is able to monitor energy expenditure information, including but not limited to step data, calorie data, speed data, distance data, pace data, acceleration data, and/or location data and to send alarm signal promptly through one of wireless ways to online user center and/or portable device application to help monitor fitness activity and motivate healthy life.

Intelligent activity recognition for a wearer, an attached sensor is able to track and record processed and/or raw data including but not limited to accelerometer data gyroscope raw data, magnetometer raw data, and/or raw data from other activity detectors, and to send promptly through one of wireless ways to online server and/or portable device application to process and recognize various activity pattern, including but not limited to walking, running, standing, seating, walking upstairs, walking downstairs, lying, jumping, field sports including but not limited to soccer, football, basketball, tennis, badminton, swimming, etc.

Sleep Monitoring

Sleep Monitoring for a wearer during sleep, an attached sensor is able to monitor sleep information including but not limited to movement, sleep posture, wakeup time, deep sleep duration, light sleep duration, and to send promptly through one of wireless ways to online user center and/or portable device application to monitor sleep quality and motivate healthy life, Organic Livestock Monitoring Daily activity monitoring for livestock, an attached sensor is able to monitor energy expenditure information, including but not limited to step data, calorie data, speed data, distance data, pace data, acceleration data, and environmental information including but not limited to temperature, ambient temperature, humility, air quality, light intensity, water quality, sound quality, and/or location data and to send alarm signal through one of wireless ways to online platform and/or portable device application to allow farmers, 3rd party, customers, to quantize and monitor organic products.

Earthquake Monitoring

Initially establish animal motion monitoring network for normal case as "database Baseline". Establishing "Earthquake active case database" during earthquake and residual earthquake for different Richter level of earthquake, and location and time dependent information. The database can include a 4-dimensional ways for each monitored selected animal: XYZ location and motion style, and Time; and/or 3-dimensional ways for sensing network: XY distribution of sensing network, and Time for dynamically tracing before (as the baseline). During and after earthquake, a living object monitoring network combining with multiple sensors located at multiple monitor sites. A database center and database network can be at a government group site, a private group site, a resident service center site, etc. Database network and monitoring network can be aligned and integrated by wire or wireless. Service center can be supported by Cloud platform, database and remote expert system to provide real time monitor earthquake. ALARM signal can be released to potential earthquake active areas to government related groups, to interested individual family and people (e.g. customers) at the critical time frame based on algorithm calculated.

Other aspects include: motion monitoring of the top portion of a skyscraper building. The top portion of a skyscraper building to monitor anti-fatigue critical stage under strong wind or earthquake. When build a new skyscraper building, based on section 4.2.1 provided valuable information, it provides valuable information for new building design to endure and minimize potential damage from strong wind or earthquake. Motion, including vibration, monitoring of safety baseline and a critical point of serious damage, broken or explosion of a mechanical module of a system, including, but not limited to, a vehicle, a ship, a submarine, an airline, a space shuttle, a nuclear power plant, a machine system or module, etc.

Life cycle and migration monitoring of a live object, including, but not limited to, animals, birds and Aquatic organisms/water products. Monitoring system include following can module a sensing network, a sensing database, a Cloud platform, a remote expert system, a service office, a control center.

Only a few examples and implementations are described. Other implementations, variations, modifications and enhancements to the described examples and implementations may be made without deviating from the spirit of the present invention. For example, the materials for the parallel upper and lower substrates, the spacer, the polymer buffed layers, and the conductive layers can be different from the examples described above while still being compatible with the disclosed invention. In some cases, the band-pass filter can be bonded with or attached to the etalon tunable filter to form a hybrid tunable filter. The disclosed hybrid tunable filters are compatible with spectral ranges for the etalon cavity and the band-pass filter (layer) other than the examples described above. The disclosed hybrid tunable filters can be applicable to tunable lasers in wavelength range other than the examples described above.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination.

It will thus be seen that the objects of the present invention have been fully and effectively accomplished. Its embodiments have been shown and described for the purpose of illustrating the functional and structural principles of the present invention and is subject to change without departure from such principles. Therefore, this invention includes all modifications encompassed within the spirit and scope of the following claims.

What is claimed is:

1. A computer-implemented method for recognizing a user's activity pattern, comprising:
   pre-storing activity data in a computer system;
   automatically determining locations of one or more sensors on a user's body;
   obtaining time series of measured activity parameters by the one or more sensors;
   automatically segmenting the time series of measured activity parameters into two or more activity periods;
   determining a spatial range of the movement in an activity period; and
   recognizing an activity in the activity period based at least in part on the measured activity parameters and the pre-stored activity data.

2. The computer-implemented method of claim 1, wherein the step of determining locations comprises:
   computing Euler angles or Quaternion angles of the one or more sensors to determine locations of one or more sensors on the user's body.

3. The computer-implemented method of claim 1, wherein the step of automatically segmenting the time series of measured activity parameters comprises:
   calculating a first average speed in a first time period;
   calculating a second average speed in a second time period; and
   separating the first period and the second period into different activity periods if a ratio of the first average speed to the second average speed is higher than a predetermined threshold.

4. The method of claim 3, wherein the predetermined threshold is between 2 and 3.

5. The computer-implemented method of claim 1, wherein the step of automatically segmenting the time series of measured activity parameters comprises:
   calculating a first average acceleration in a first time period;
   calculating a second average acceleration in a second time period; and
   separating the first period and the second period into different activity periods if a ratio of the first average acceleration to the second average acceleration is higher than a predetermined threshold.

6. The method of claim 1, wherein the activity is recognized in the activity period based in part on the spatial range of the movement in the activity period.

7. The method of claim 1, further comprising:
   extracting a signature pattern using the time series of measured activity parameters,
   wherein the activity data pre-stored in the computer system comprise a plurality of signature patterns each corresponding to a known activity,
   wherein the activity in the activity period is recognized in part by matching the signature pattern extracted using the time series of measured activity parameters to the one of the plurality of signature patterns stored in the computer system.

8. The method of claim 7, wherein the signature pattern is personalized and specific to the user's behavior in the activity.

9. The method of claim 1, wherein the measured activity parameters comprise movement parameters including positions, displacements, distances, speeds, angular velocities, or altitude, physiological parameters including body temperature, heart rate, pulse rate, beat-to-beat heart variability, blood pressure, body fat, or calorie, or environmental characteristics including such as ambient temperature, humility, air quality, light intensity, water quality, sound quality, location.

10. The method of claim 1, wherein the activity recognized in the activity period comprises walking, running, stair climbing, mountain climbing, hiking, driving, taking elevator, dancing, playing soccer, basketball, tennis or ping pong, swimming, diving, sleeping, sitting, driving, jumping, or rotating.

11. The method of claim 1, further comprising:
based on the activity recognized in the activity period, sending control data from the computer system to control an actuator in the sensor, which guides the user to adjust his or her movements.

12. The method of claim 11, wherein the actuator is configured to produce sound, music, voice, light, vibrations, or heat to guide the user to adjust his or her movements.

13. A computer system for recognizing a user's activity pattern, comprising:
one or more sensors configured to be worn on a user's body and to obtain time series of measured activity parameters;
a computer storage configured to store activity data;
a computer processor configured to automatically determine locations of the one or more sensors on the user's body, wherein the computer processor is configured to automatically segment the time series of measured activity parameters into two or more activity periods, to determine a spatial range of the movement in an activity period, and to recognize an activity in the activity period based at least in part on the measured activity parameters and the pre-stored activity data.

14. The computer system of claim 13, wherein the computer processor is configured to compute Euler angles or Quaternion angles of the one or more sensors to determine locations of one or more sensors on the user's body.

15. The computer system of claim 13, wherein the computer processor is configured to:
calculating a first average speed in a first time period;
calculating a second average speed in a second time period; and
separating the first period and the second period into different activity periods if a ratio of the first average speed to the second average speed is higher than a predetermined threshold.

16. The computer system of claim 15, wherein the predetermined threshold is between 2 and 3.

17. The computer system of claim 13, wherein the computer processor is configured to:
calculate a first average acceleration in a first time period;
calculate a second average acceleration in a second time period; and
separate the first period and the second period into different activity periods if a ratio of the first average acceleration to the second average acceleration is higher than a predetermined threshold.

18. The computer system of claim 13, wherein the activity is recognized in the activity period based in part on the spatial range of the movement in the activity period.

19. The computer system of claim 13, wherein the computer processor is configured to extract a signature pattern using the time series of measured activity parameters,
wherein the activity data pre-stored in the computer system comprise a plurality of signature patterns each corresponding to a known activity,
wherein the activity in the activity period is recognized in part by matching the signature pattern extracted using the time series of measured activity parameters to the one of the plurality of signature patterns stored in the computer system.

20. The computer system of claim 19, wherein the signature pattern is personalized and specific to the user's behavior in the activity.

* * * * *